United States Patent
Domracheva et al.

(10) Patent No.: US 10,748,651 B2
(45) Date of Patent: Aug. 18, 2020

(54) METHOD AND SYSTEM OF TEETH ALIGNMENT BASED ON SIMULATING OF CROWN AND ROOT MOVEMENT

(71) Applicant: Dommar LLC, Moscow (RU)

(72) Inventors: Marina Evgenievna Domracheva, Moscow (RU); Fedor Alexandrovich Aptekarev, Moscow (RU)

(73) Assignee: Dommar LLC, Moscow (RU)

( * ) Notice: Subject to any disclaimer, the term of this patent is extended or adjusted under 35 U.S.C. 154(b) by 0 days.

(21) Appl. No.: 16/017,687

(22) Filed: Jun. 25, 2018

(65) Prior Publication Data
US 2019/0148005 A1 May 16, 2019

(30) Foreign Application Priority Data

Nov. 16, 2017 (EA) .................................. 201700561

(51) Int. Cl.
| | | |
|---|---|---|
| *G06T 17/20* | (2006.01) | |
| *G16H 30/40* | (2018.01) | |
| *G06K 9/62* | (2006.01) | |
| *G16H 20/40* | (2018.01) | |
| *G16H 50/50* | (2018.01) | |

(52) U.S. Cl.
CPC ............ *G16H 30/40* (2018.01); *G06K 9/628* (2013.01); *G06K 9/6256* (2013.01); *G06T 17/20* (2013.01); *G16H 20/40* (2018.01); *G16H 50/50* (2018.01); *G06K 2209/05* (2013.01); *G06T 2200/08* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 7,585,172 B2 | 9/2009 | Rubbert et al. | |
| 2004/0073417 A1* | 4/2004 | Rubbert ................... | A61C 7/00 703/11 |
| 2013/0051516 A1 | 2/2013 | Yang et al. | |
| 2014/0037180 A1* | 2/2014 | Wang ................... | A61B 5/0088 382/132 |
| 2014/0314291 A1 | 10/2014 | Souza et al. | |
| 2017/0213339 A1 | 7/2017 | Hibbard et al. | |

FOREIGN PATENT DOCUMENTS

| | | |
|---|---|---|
| RU | 132340 U1 | 9/2013 |
| RU | 2495642 C2 | 10/2013 |
| RU | 2559762 C1 | 8/2015 |
| WO | 2011/103876 A1 | 9/2011 |

OTHER PUBLICATIONS

Miki et al., "Classification of Teeth in Cone-Beam CT using Deep Convolutional Neural Network" 2016. (Year: 2016).*
International Search Report issued in International Patent Application No. PCT/RU2018/050065 dated Sep. 20, 2018, 7 pages.

* cited by examiner

*Primary Examiner* — Nicholas R Wilson
(74) *Attorney, Agent, or Firm* — Oblon, McClelland, Maier & Neustadt, L.L.P.

(57) ABSTRACT

The present disclosure relates to a dental image processing protocol for the design of dental aligners. Specifically, the dental image processing protocol aids in the determination of tooth movements during realignment, based on an initial position and a final position, and on characteristics of the periodontal environment. Therefore, planned tooth movements reflect both crown movement and root movement within biological structures of the alveolar process.

11 Claims, 16 Drawing Sheets
(7 of 16 Drawing Sheet(s) Filed in Color)

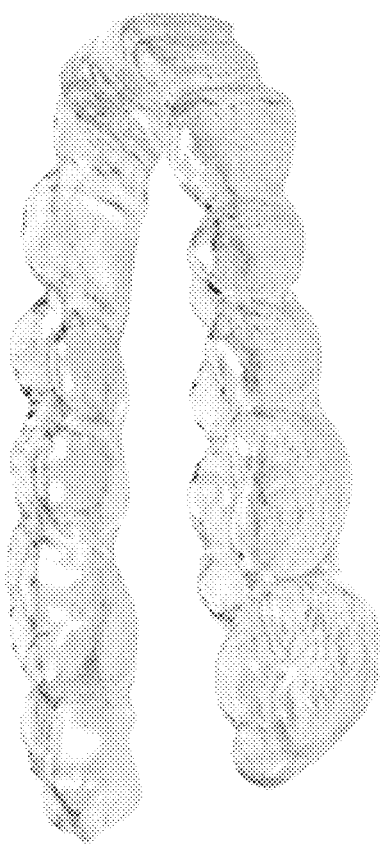
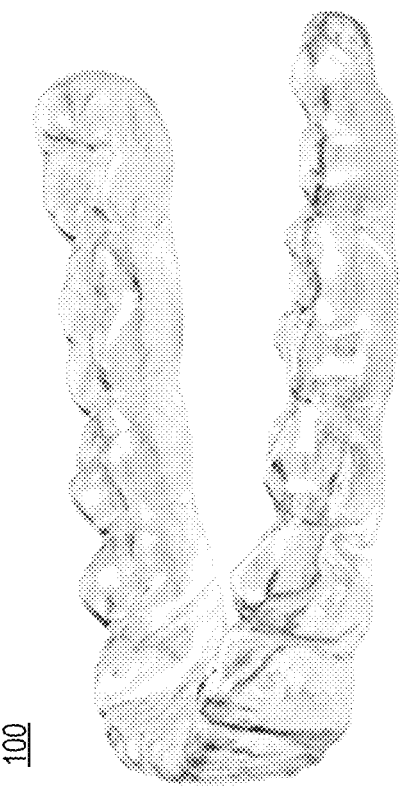
FIG. 1

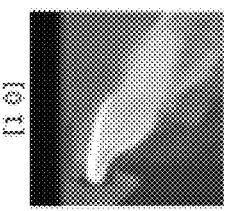
FIG. 7A
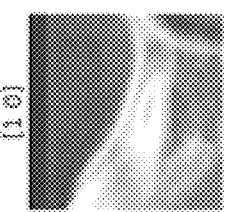
FIG. 7B
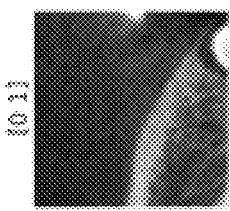
FIG. 7C
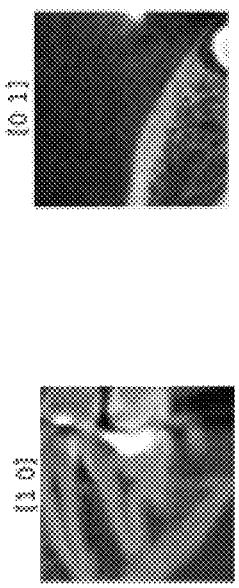
FIG. 7D
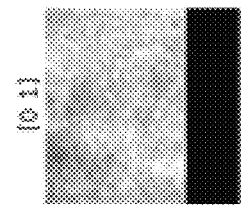
FIG. 7E
FIG. 7F
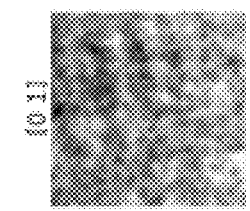
FIG. 7G
FIG. 7H
FIG. 7I
FIG. 7J
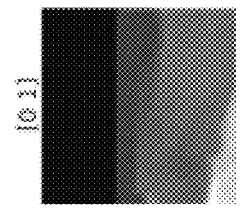
FIG. 7K
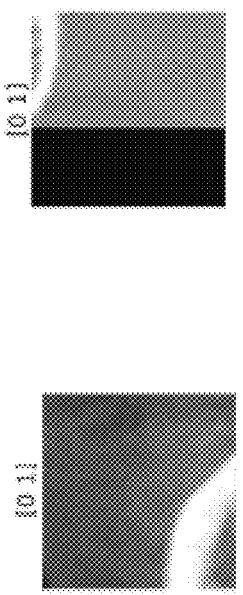

S731

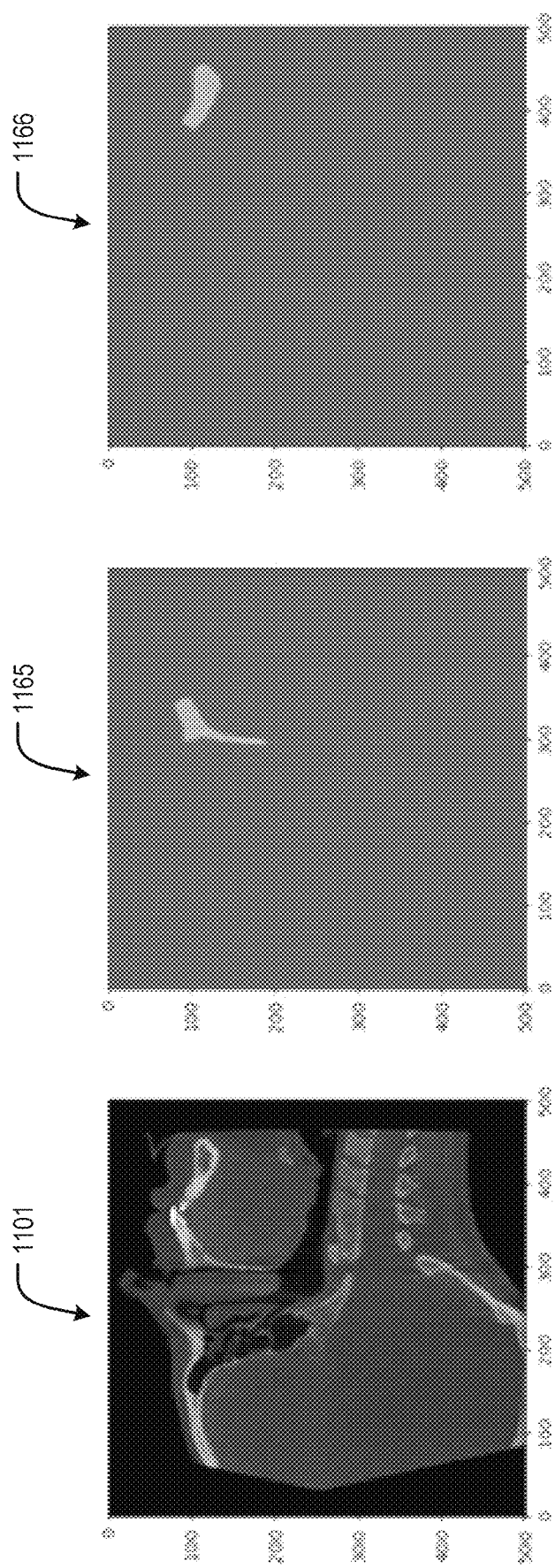

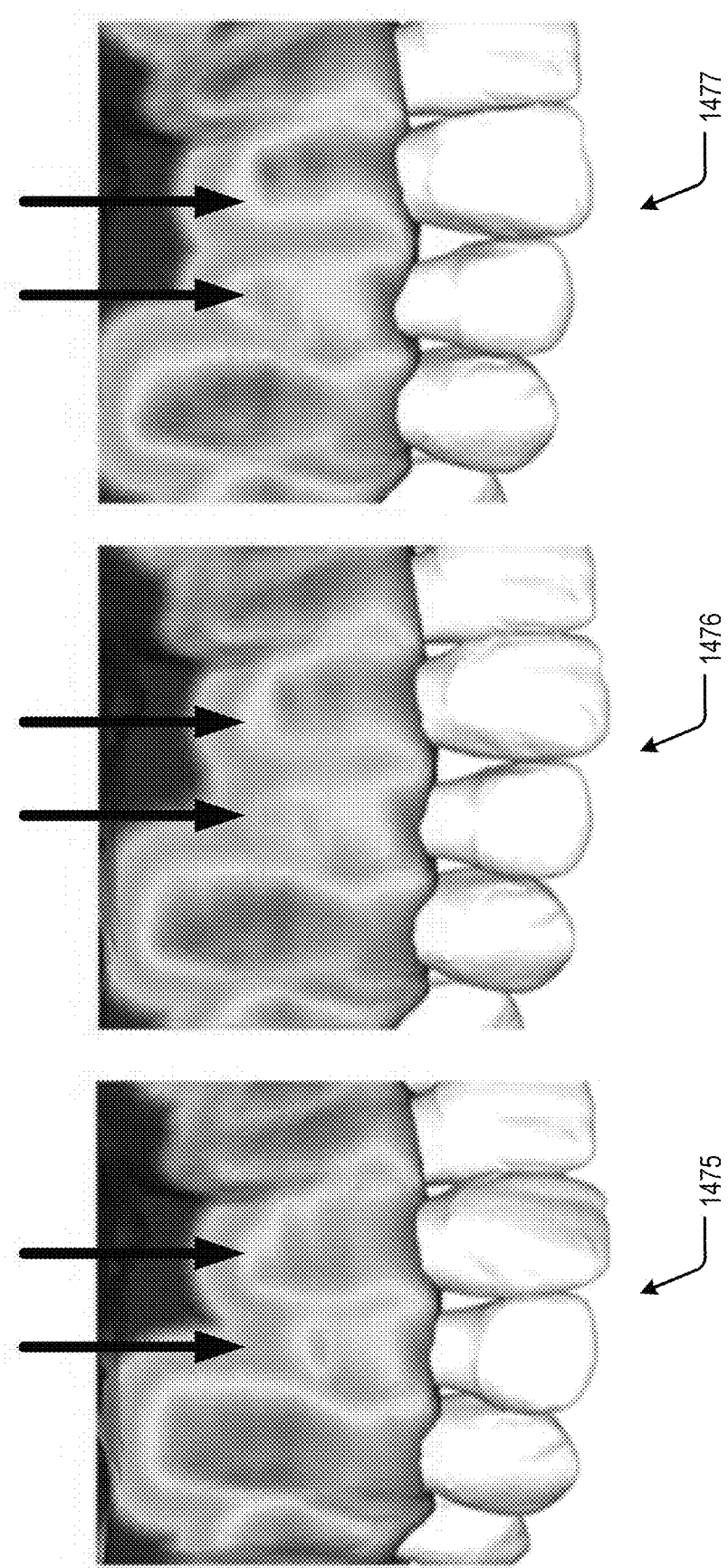

ent of the present disclosure;

METHOD AND SYSTEM OF TEETH ALIGNMENT BASED ON SIMULATING OF CROWN AND ROOT MOVEMENT

CROSS-REFERENCE TO RELATED APPLICATIONS

This application claims priority to Eurasian Patent Application No. 201700561 filed Nov. 16, 2017, the content of which is hereby incorporated herein by reference in its entirety.

BACKGROUND

Field of the Disclosure

The present disclosure relates to a dental image processing protocol for the design of dental aligners.

Description of the Related Art

Orthodontics, generally, and dental alignment, in particular, is a well-developed area of dental care. For patients with maligned teeth, traditional braces or, more recently, clear aligners, offer a strategy for improved dental function and aesthetics though gradual teeth movements. These gradual teeth movements slowly move a crown of a tooth until a desired final position is reached. These approaches, however, fail to appropriately consider the impact of corresponding root movements, in the context of surrounding soft and hard tissues, on the final position of the crown, focusing instead on an aesthetically and functionally ideal crown position. An approach for determining crown position that adequately incorporates the impact of root movement and the root environment has yet to be developed.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to a method, apparatus, and computer-readable medium comprising a processing circuitry configured to classify pixels of one or more medical images into classes corresponding to biological structure types, segment the classified pixels of the one or more medical images into biological structures, render a three-dimensional model of the biological structures based on the segmented classified pixels, determine one or more metrics, based upon the three-dimensional model, describing a bone of the biological structures, acquire a final position of each of the one or more teeth of the dental arch based upon the three-dimensional model, and generate the intermediate position of each of the one or more teeth of the patient based upon the one or more metrics and the acquired final position.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

The patent or application file contains at least one drawing executed in color. Copies of this patent or patent application publication with color drawing(s) will be provided by the office upon request and payment of the necessary fee.

A more complete appreciation of the disclosure and many of the attendant advantages thereof will be readily obtained as the same becomes better understood by reference to the following detailed description when considered in connection with the accompanying drawings, wherein:

FIG. 1 is an illustration of dental aligners, according to an embodiment of the present disclosure;

FIG. 7A is an illustration of an exemplary pixel patch of a dental image processing protocol, according to an embodiment of the present disclosure;

FIG. 7B is an illustration of an exemplary pixel patch of a dental image processing protocol, according to an embodiment of the present disclosure;

FIG. 7C is an illustration of an exemplary pixel patch of a dental image processing protocol, according to an embodiment of the present disclosure;

FIG. 7D is an illustration of an exemplary pixel patch of a dental image processing protocol, according to an embodiment of the present disclosure;

FIG. 7E is an illustration of an exemplary pixel patch of a dental image processing protocol, according to an embodiment of the present disclosure;

FIG. 7F is an illustration of an exemplary pixel patch of a dental image processing protocol, according to an embodiment of the present disclosure;

FIG. 7G is an illustration of an exemplary pixel patch of a dental image processing protocol, according to an embodiment of the present disclosure;

FIG. 7H is an illustration of an exemplary pixel patch of a dental image processing protocol, according to an embodiment of the present disclosure;

FIG. 7I is an illustration of an exemplary pixel patch of a dental image processing protocol, according to an embodiment of the present disclosure;

FIG. 7J is an illustration of an exemplary pixel patch of a dental image processing protocol, according to an embodiment of the present disclosure;

FIG. 7K is an illustration of an exemplary pixel patch of a dental image processing protocol, according to an embodiment of the present disclosure;

FIG. 11A is an illustration of a source image of a segmentation of bone of a dental image, according to an embodiment of the present disclosure;

FIG. 11B is an illustration of a segmentation of bone of a dental image, according to an embodiment of the present disclosure;

FIG. 11C is an illustration of a segmentation of bone of a dental image, according to an embodiment of the present disclosure;

FIG. 14A is an illustration of a three-dimensional model of an initial tooth position, according to an embodiment of the present disclosure;

FIG. 14B is an illustration of a three-dimensional model of an intermediary tooth position, according to an embodiment of the present disclosure;

FIG. 14C is an illustration of a three-dimensional model of a final tooth position, according to an embodiment of the present disclosure.

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Currently, orthodontist and dental technicians develop teeth movement plans based upon initial and ideal final crown positions. Considering only teeth crowns, however, ignoring root movements and the root environment, makes it possible that root collisions or other damage may occur to the tooth or surrounding bone tissue at intermediary tooth positions. In an example, an intermediary tooth position may result in collision of the roots of adjacent teeth. In another example, a thickness of the alveolar process, the bone tissue surrounding a tooth root, can limit the ability of the tooth root to move to an intermediary step. When the surrounding bone tissue is of insufficient thickness, a realizable movement of a tooth may be less than an ideal movement of the tooth, resulting in impaired treatment and sub-optimal teeth function and aesthetic. In yet another example, varying densities of periodontal bone can impact potential root movements and realignment, thereof.

Based upon the insufficiencies of current methodologies, the present disclosure describes an orthodontic treatment approach that considers an evaluation of the condition of the tissues surrounding the tooth and the alveolar process, in particular. Moreover, the evaluation of the condition of the tissues surrounding the tooth is patient-specific, reflecting the unique density and thickness of an individual patient's periodontal bone.

Figure 2:
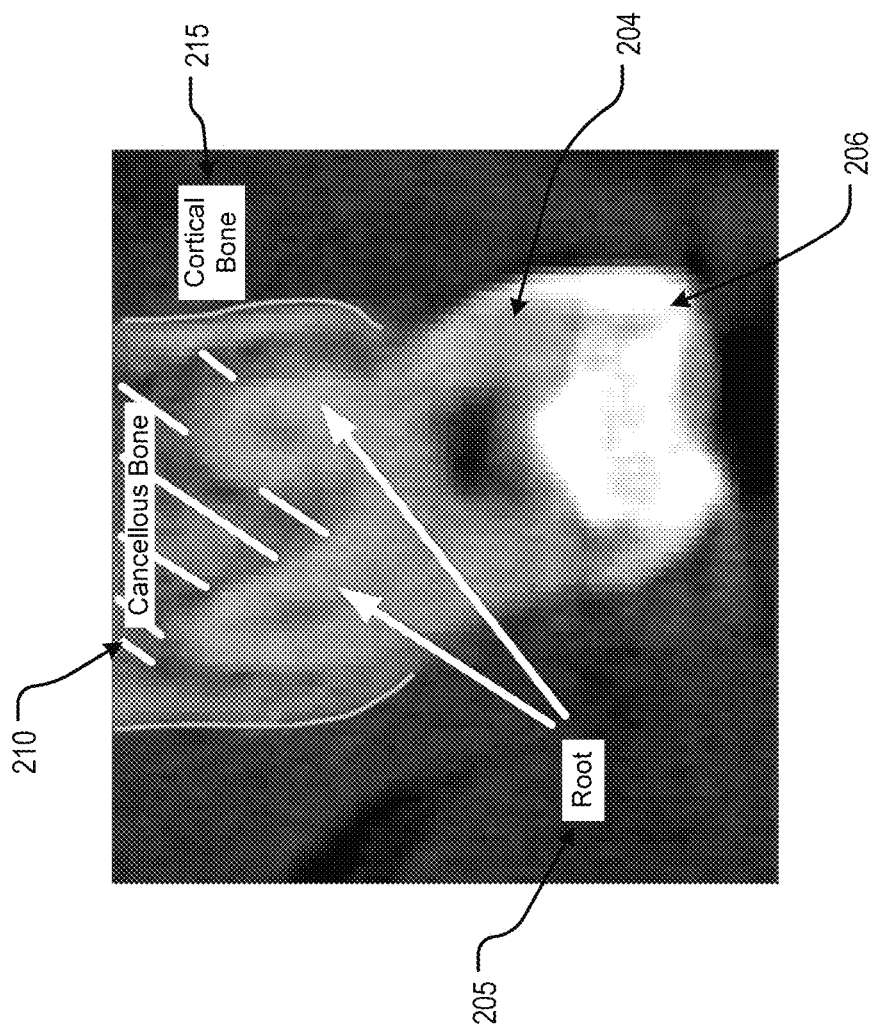
FIG. 2 is an illustration of a dental image of a tooth, according to an embodiment of the present disclosure.

FIG. 1 is an illustration of dental aligners, according to an embodiment of the present disclosure. Following a determination of an initial tooth position and a realizable final tooth position, intermediary tooth movements can be determined and dental aligners 100 can be fabricated, accordingly, to slowly move and realign a patient's teeth. Oftentimes, however, as described above, these determinations are based only upon an ideal final tooth position and the position of the crown of the tooth relative to adjacent teeth, which can lead to root, periodontal ligament, or periodontal bone damage upon movement. In order to incorporate information related to the environment of the tooth and surrounding tissues during dental aligner 100 fabrication, an approach for identifying tissue-types, generating three-dimensional (3D) models, and determining periodontal tissue characteristics, thereof, is required. To this end, it becomes necessary to develop a strategy for discerning soft tissues from hard tissues and tooth roots from surrounding bone of varying densities. FIG. 2 is an illustration of a dental image of a tooth, according to an embodiment of the present disclosure. In an embodiment, a dental image of a tooth may be but is not limited to an image acquired via intraoral optical imaging, impressions, dental models, ultrasound, or radiography. In an example, a plurality of images, or slices, may be acquired via radiography and reconstructed to render a 3D model. With reference again to FIG. 2, a tooth 204 comprises a crown 206 and one or more roots 205. The one or more roots 205 are resident within an alveolar process, a thickened ridge of bone containing dental alveoli, or tooth sockets. The alveolar process is comprised of cortical bone 215, a compact, relatively dense bone, and cancellous bone 210, a spongy, relatively porous bone. Together, cortical bone 215 and cancellous bone 210 provide a strong foundation from which the one or more roots 205 of the tooth 204 are anchored. As related to the present disclosure, cortical bone 215 and cancellous bone 210, as periodontal tissues, contribute to the determination of possible movements of a tooth.

In planning a tooth movement such that the tooth and periodontal environment are considered concurrently, a variety of structures, including the above-described features, must be identified. Moreover, once these features have been identified for a single two-dimensional (2D) dental image, the same can be performed for additional 2D dental images, or slices, until a 3D model can be rendered, therefrom. In addition to providing for aesthetic evaluation, a 3D model synthesizes information regarding periodontal tissue density and thickness, thereby bounding possible tooth movements and providing a prescribing dental professional a tool from which to determine a tooth movement. The process alluded to above is described in FIG. 3, a flowchart of a dental image processing protocol implemented via a dental image processing device comprising a processing circuitry.

According to an embodiment of the present disclosure, the dental image processing protocol described herein can be appreciated in context of a full dental arch or an individual tooth. Initially, digital representations of an initial position of a patient's teeth must be acquired. A variety of techniques including but not limited to impressions, dental scanner of impressions or dental models, intraoral scanners for digital impressions, intraoral X-ray, ultrasound, and computed tomography can be used individually or in combination to acquire digital representations of the initial position of the patient's teeth. In an embodiment of the present disclosure, in order to create a digital impression, an intraoral scanner S341 may be employed to acquire topographical characteristics of crowns of the teeth. The intraoral scanner may employ a modality selected from a group including but not limited to lasers, infrared light, and structured light. So that tooth movements can be determined in the context of crowns and roots, a radiographic imaging modality may be employed in order to acquire spatial information relating to the roots and periodontal tissues, including soft tissues and hard tissues (e.g. alveolar process). In an embodiment, the radiographic imaging modality may be selected from the group including but not limited to projection radiography, computed tomography (CT), dual energy X-ray absorptiometry, fluoroscopy, and contrast radiography. In an example, the radiographic imaging modality may be cone beam computed tomography (CBCT) S350. Radiographic images may comprise multi-planar radiographic images including but not limited to sagittal, transverse, and coronal. It should be appreciated that, apart from radiographic techniques, a variety of imaging modalities including but not limited to ultrasound may be used for acquisition of images describing spatial information of the roots and periodontal tissues.

Following acquisition of a plurality of dental images of a patient via CBCT, various biological structures, including the teeth and the jaw, must be digitally identified so that they can be later incorporated into a holistic 3D model of the dental environment. As an alternative to manual classification of individual biological structures of a plurality of dental images, the present disclosure employs a machine learning approach, a platform for rapid evaluation of the plurality of dental images, to classify the various biological structures of each dental image of a patient S351. In an exemplary embodiment, the machine learning approach may be a fully convolutional neural network (FCN). Unlike similar approaches that perform patch-wise predictions, an FCN classifier evaluates and predicts the classification of each pixel of an unknown image. Per-pixel classification allows the resulting predictions to be segmented into multiple tissue classes S352, combining adjacent pixels of similar classification and density and defining the shape of each type of tissue, or biological structure, as building blocks for a 3D model. In turn, via a surface reconstruction technique such as, for instance, marching cubes, each of the plurality of classified and segmented dental images of a patient are combined and reconstructed to form a 3D model of dentition, including a patient's dental arches and surrounding tissues S353. In an exemplary embodiment, the surface reconstruction technique may be selected from a group including but not limited to marching tetrahedrons and marching cubes, a sequential surface rendering model wherein a polygonal mesh is fitted to a surface interacting with pixels from adjacent slices.

The reconstructed surfaces can then be integrated into the digital impressions acquired via intraoral 3D imaging to create a simple 3D model of the mouth of a patient S343, including crowns, roots and periodontal tissues. In an embodiment, this data integration may be accomplished via point-based alignment of two surface models, an interactive method of registration of polygonal meshes. First, at least three corresponding points on each of the two surface models are selected. Next, a transformation matrix is computed and applied via translation and rotation or quaternion. If the resulting overlap between the two surface models is greater than a pre-determined threshold, a new transformation matrix must be determined and applied such that the resulting overlap between the two surface models is less than the pre-determined threshold. In an exemplary embodiment, the at least three corresponding points on each of the two surface models are selected manually. In another embodiment, corresponding points on each of the two surface models may be selected automatically via software, wherein the corresponding points are features selected from a group including but not limited to cusps, gloves, offsets and pits of molars, or central points of cutting edges on incisors.

Concurrently, in order to better define the periodontal environment of the simple 3D model and provide a realistic model of potential tooth and root movement, characteristics of the alveolar process must be determined. To this end, a density measurement S354 and a distance measurement S355 of the periodontal space may be computed from the surface reconstruction, or simple 3D model, of the classified and segmented predictions. The density measurement comprises computing, from each point on a mesh describing the surface of a root, a metric of the density of the surrounding tissue. This metric may be determined on the basis of mean voxel intensities surrounding a vertex-point coordinate of the segmentation, reflecting the spatial qualities of bone and the ability of a tooth to move, therein. The distance measurement comprises computing, for each point on the mesh describing the surface of a bone, such as the buccal surface of the alveolar bone, a distance to a nearest point on the mesh describing the root. This distance, therefore, reflects a volume of the alveolar process wherein a tooth may move.

Once calculated for each point within the mesh, or model, the density measurement and distance measurement may be mapped to the simple 3D model, creating a complex 3D model S356. To allow for rapid visualization of the distance measurement, varying distances are denoted via heat map, wherein regions of minimal thickness and regions of maximal thickness are represented with varying colors.

Figure 4:
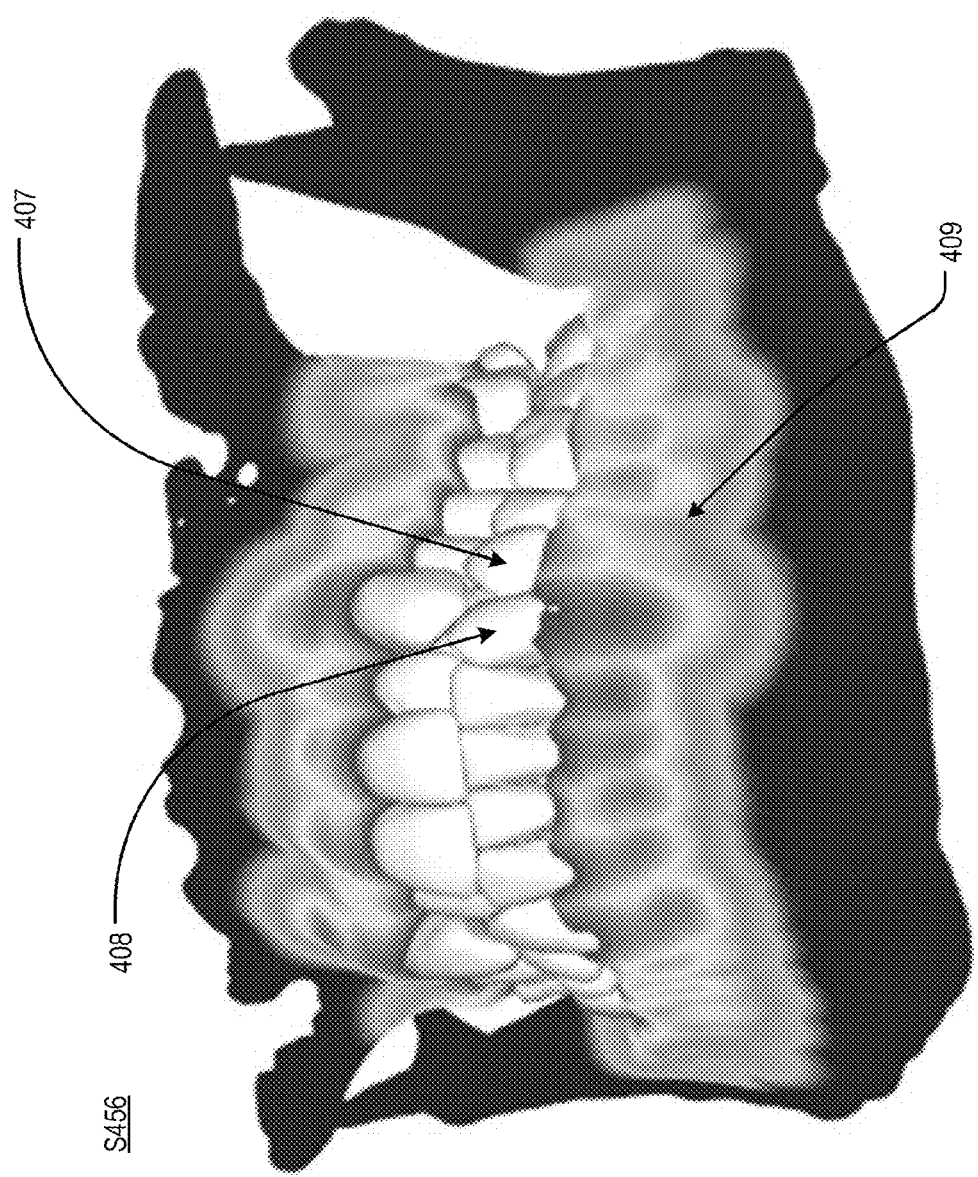
FIG. 4 is an illustration of a complex three-dimensional model generated from a plurality of processed dental images and annotated with a surface heat map, according to an embodiment of the present disclosure.

Having now generated a complex 3D model of a patient's mouth, including dental arches and alveolar process, annotated to denote tissue thicknesses and densities, the complex 3D model may be manipulated to determine realizable final tooth positions S360. In doing so, intermediary tooth positions and movements necessary to achieve such positions may be determined. FIG. 4 is an illustration of a complex 3D model generated from a plurality of processed dental images, annotated with a surface heat map, according to an embodiment of the present disclosure.

As described above, following acquisition and processing of intraoral 3D scans and radiographic images, surface mesh data may be integrated to create a 3D model of an initial position of the dental arches of a patient. A heat map, overlaid on the 3D model, indicates local thicknesses of the alveolar process, the periodontal environment therein varying across individual teeth of the dental arches. For example, with reference to FIG. 4, a canine 408 and an adjacent premolar 407 have disparate local periodontal environments. The canine 408 may be positioned closer to a buccal surface of an alveolar process 409, as indicated by a darker shade, intense red, while the premolar 407 may be positioned posteriorly with respect to the buccal surface of the alveolar process 409, proximate to a lingual surface of the alveolar process 409, as indicated by light shades of the heat map. This heat map feature allows a prescribing dental professional to visualize possible and impossible tooth movements and select appropriate intermediary movements within skeletal constraints.

Figure 5:
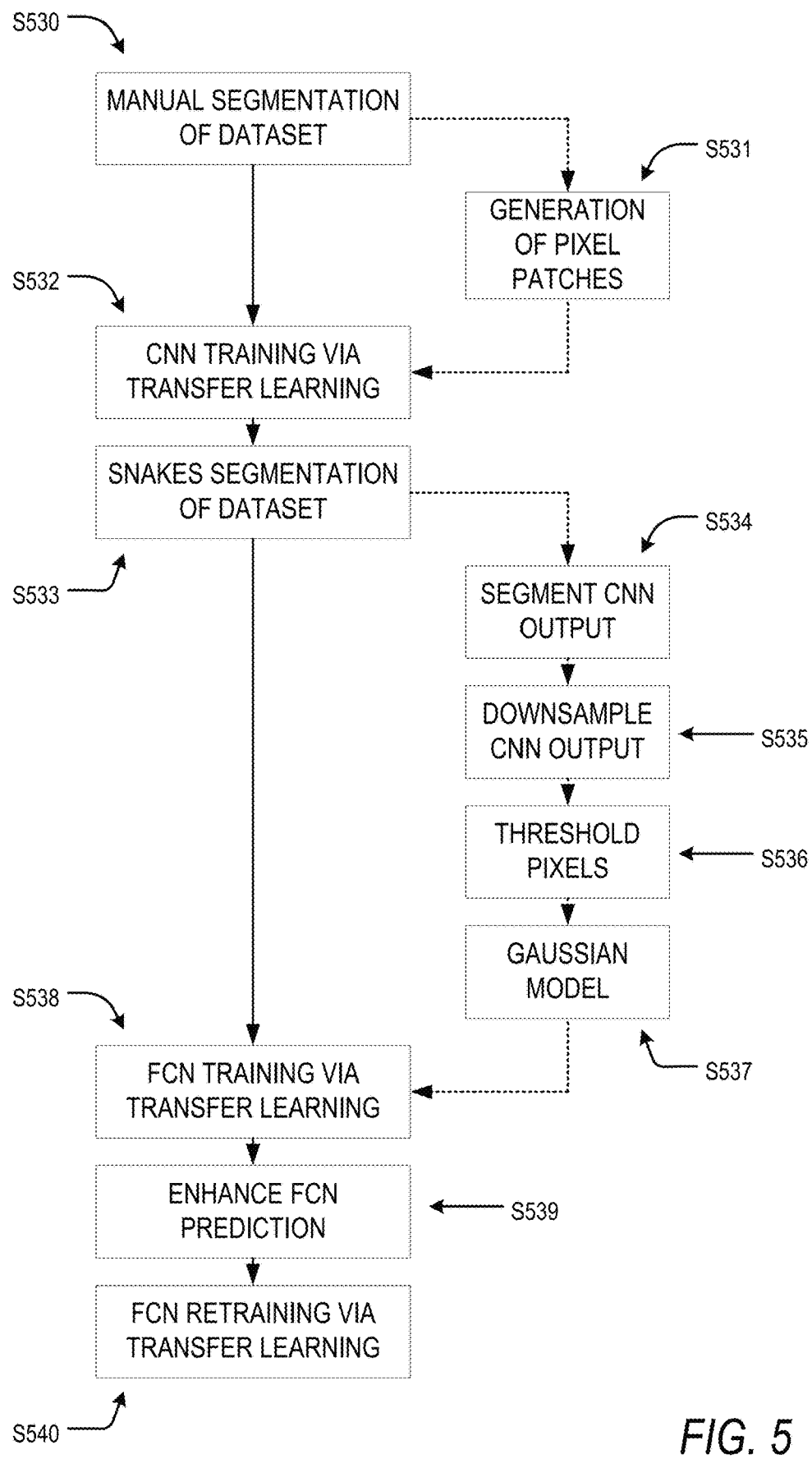
FIG. 5 is a flowchart of an aspect of a training protocol of a dental image processing protocol, according to an embodiment of the present disclosure.

Critical to the success of the dental image processing protocol is the ability to accurately classify biological structures, or tissues, of dental images, and radiographic slices, in particular. To this end, FIG. 5 is a flowchart of an aspect of a training protocol of a classification approach of a dental image processing protocol, according to an embodiment of the present disclosure. Generally, the training approach prepares an FCN classifier to be applied to the binary classification of 'bone' or the binary classification of 'teeth'. Specifically, the training approach provides annotated training data, manually or automatically generated, directed to the above-described classes. In an example, when applied, the FCN classifier is meant to predict, for each pixel of a slice, class 1 if a tooth is present and class 0 if a tooth is not present.

The process of generating the annotated training data is described in FIG. 5. Generally, the annotated training data may be based, in part, on combinations of pixel intensities that are considered visual features. Initially, from a first dataset comprising a plurality of CBCT dental images, a manual segmentation tool may be applied in order to label the 'tooth' pixels S530. In an embodiment, the manual segmentation tool can be a 'brush tool'. Following manual labeling of 'tooth' of each pixel of each dental image of the dataset, a pretrained convolutional neural network (CNN), referred to herein as "retrained CNN", and CNN classifier therein, may be trained to perform per pixel predictions of 'tooth' based upon the labeled images of the first dataset. In an embodiment, the pretrained CNN classifier can be based on AlexNet. In another embodiment, the pretrained CNN classifier can be further tuned according to a plurality of labeled pixel patches S532. To this end, the pixel-wise manually segmented dental images described above are converted to a plurality of pixel patches S531, wherein each of the plurality of generated pixel patches may comprise 120 pixels surrounding a central pixel. Compared with pixel-wise training, patch-wise training decreases training time without unnecessarily sacrificing resulting classification accuracy.

Following training, the retrained CNN classifier may be applied to a second dataset comprising a plurality of CBCT dental images. In order to prepare the resulting retrained CNN classifier predictions for active contour modeling, or snakes segmentation S533, the retrained CNN classifier predictions can be converted to segmentations S534. The segmented predictions may then be downsampled to obtain prepared images for snakes segmentation S535, a framework in computer vision for delineating an object outline from a 2D image. To this end, pixels of the dental images may first be thresholded according to Hounsfield units (HU), wherein HU values reflect the radiodensity of a biological structure S536. Table 1 describes exemplary HU thresholding values, according to an exemplary embodiment of the present disclosure. Every second pixel may be taken into a sample dataset to generate a Gaussian model estimator for given biological structure types, or classes S537, thus providing a speed-map for snakes segmentation. The above-described

TABLE 1

Radiodensity Assignments

| Label | Tissue Type | Radiodensity (HU) |
|---|---|---|
| #0 | Clear | <−990 HU |
| #1 | Teeth | Segmented by CNN |
| #2 | Bone | Not teeth > 650 HU |
| #3 | Soft tissue | 0 HU < not teeth < 650 HU |
| #4 | Liquids | −800 HU < not teeth < 0 HU | snakes segmentation may be performed as a final segmentation of the modified output of the retrained CNN classifier. The resulting plurality of CBCT dental images segmented via snakes segmentation form an initial FCN training database. The initial FCN training database can then be used to retrain a pretrained Unet-FCN S538, referred to herein as "retrained FCN", and an FCN classifier therein. In an embodiment, false pixels adjacent to two true pixels may have added weight.

In order to evaluate the predictive value of the retrained FCN classifier, and improve its future predictive power, the initial FCN training database can be continuously updated through a process of 3D prediction enhancement S539. Broadly, the 3D prediction enhancement process follows a similar, run-time, process employed for unknown images during implementation of the retrained FCN classifier. First, predictions of the initial FCN training database by the retrained FCN classifier may be segmented. These segmentations may then be converted to a 3D polygonal surface. This allows for enhancement of the 3D surface model at a holistic level and with focus on the result, eliminating the laborious task of enhancing individual slices of the 3D polygonal surface. Once enhanced, the 3D polygonal surface model can then be converted back into segmentation and, upon confirming the segmentation quality, returned to a subsequent FCN training database.

Specifically, 3D prediction enhancement comprises surface reconstruction via marching cubes, for instance, followed by manual adjustments to apply filters and correct prediction errors in the reconstructed surface. With manual adjustments completed at the level of the 3D model, the surface may be re-segmented into 2D slices and returned to the initial FCN training database, thus forming the subsequent training database. When the subsequent FCN training database has doubled in size, the retrained FCN classifier may be further retrained on the enhanced, subsequent FCN training database S540 in order to further improve classification accuracy. As described, the above process may be iterative.

According to an embodiment, the initial FCN training database and subsequent FCN training databases, therefrom, comprise approximately 50,000 dental images, based upon the quality of the produced data. The enhancement and retraining process may be repeated when an FCN training database doubles in size, the dental images with lowest prediction quality being enhanced, as described above, and the FCN classifier being retrained in order to adjust prediction quality.

Each of the steps of the above-described training protocol will be further discussed below.

Figure 6B:
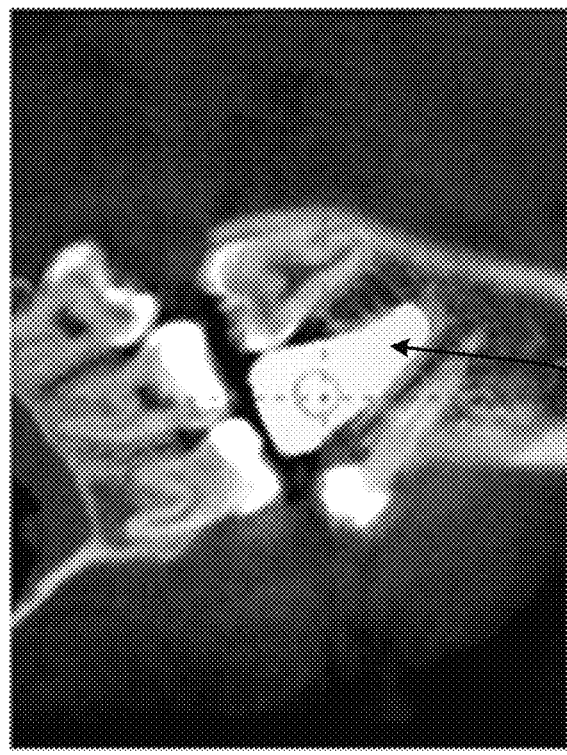
FIG. 6B is an illustration of an aspect of a manually-segmented dental image of a tooth, according to an embodiment of the present disclosure.
Figure 6A:
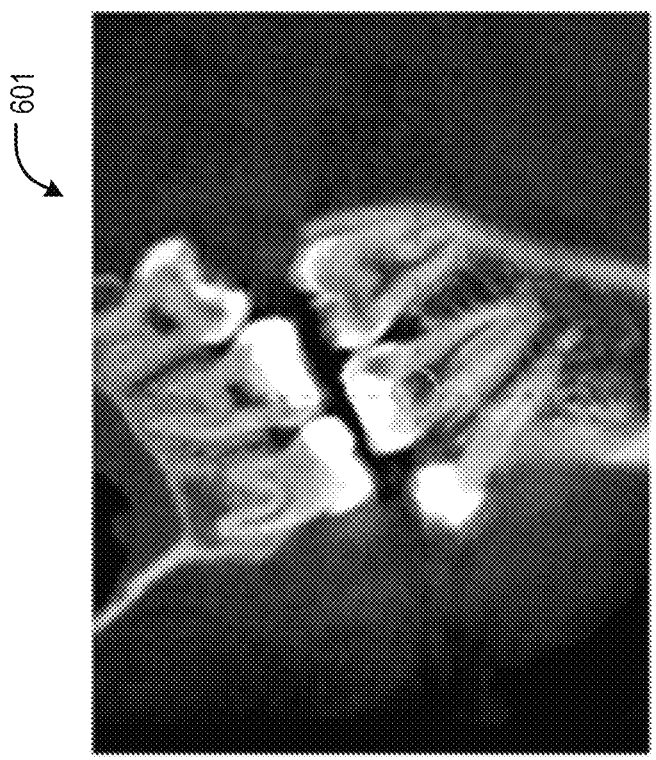
FIG. 6A is an illustration of an aspect of a manually-segmented dental image of a tooth, according to an embodiment of the present disclosure.

FIG. 6A and FIG. 6B are illustrations of an aspect of a manually-segmented dental image of a tooth. According to an embodiment of the present disclosure, a source image 601 from a first dataset comprising the plurality of CBCT dental images, shown in FIG. 6A, may be manually segmented. Through manual segmentation, the user is able to manually assign labels to each pixel, a process creating ground truth data for training semantic segmentation protocols. In FIG. 6B, a manual segmentation via 'brush tool' S630, for instance, allows for exact identification and assignment of a 'tooth' label to appropriate pixels of the source image 601. In another embodiment, the manual segmentation tool may be selected from a group including but not limited to flood fill tool, smart polygon tool, and polygon tool.

Figure 7L:
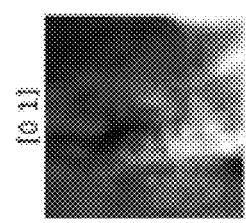
FIG. 7L is an illustration of an exemplary pixel patch of a dental image processing protocol, according to an embodiment of the present disclosure.
Figure 7M:
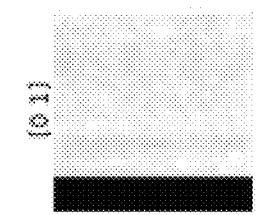
FIG. 7M is an illustration of an exemplary pixel patch of a dental image processing protocol, according to an embodi
Figure 7N:
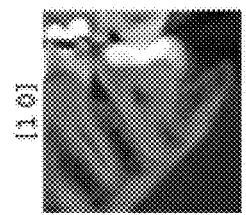
- FIG. 7N is an illustration of an exemplary pixel patch of a dental image processing protocol, according to an embodiment of the present disclosure.
Figure 7O:
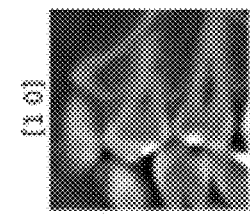
FIG. 7O is an illustration of an exemplary pixel patch of a dental image processing protocol, according to an embodiment of the present disclosure.
Figure 7P:
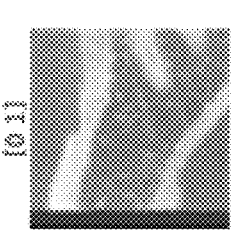
FIG. 7P is an illustration of an exemplary pixel patch of a dental image processing protocol, according to an embodiment of the present disclosure.
Figure 7Q:
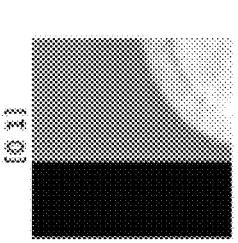
FIG. 7Q is an illustration of an exemplary pixel patch of a dental image processing protocol, according to an embodiment of the present disclosure.
Figure 7R:
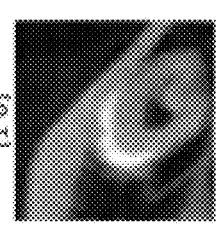
FIG. 7R is an illustration of an exemplary pixel patch of a dental image processing protocol, according to an embodiment of the present disclosure.
Figure 7S:
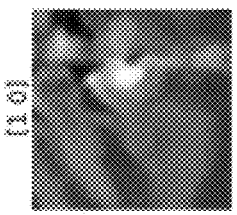
FIG. 7S is an illustration of an exemplary pixel patch of a dental image processing protocol, according to an embodiment of the present disclosure.
Figure 7T:
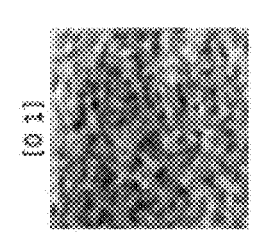
FIG. 7T is an illustration of an exemplary pixel patch of a dental image processing protocol, according to an embodiment of the present disclosure.
Figure 7U:
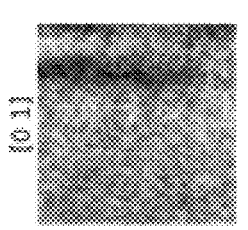
FIG. 7U is an illustration of an exemplary pixel patch of a dental image processing protocol, according to an embodiment of the present disclosure.

Following manual labeling of 'tooth' of each pixel of each dental image of the first dataset, the first dataset may be used to train a pretrained CNN classifier, such as, for instance, AlexNet, to perform per pixel predictions of 'tooth'. In an embodiment, the pretrained CNN classifier may be further tuned according to a plurality of labeled pixel patches. To this end, the manually segmented dental images described above may be converted to a plurality of pixel patches S531, wherein each of the plurality of generated pixel patches comprises 120 pixels surrounding a central pixel. Using pixel patches instead of individual pixels decreases training time without unnecessarily sacrificing classification accuracy. FIG. 7A through FIG. 7U are illustrations of exemplary pixel patches of a dental image processing protocol, according to an embodiment of the present disclosure. The pretrained CNN classifier may be retrained on pixel patches from the 'tooth' class S731, as illustrated in FIG. 7A through FIG. 7U and wherein [1 0] indicates 'tooth' and [0 1] indicates 'not tooth', in order to predict whether the central pixel of each pixel patch belongs to the 'tooth' class.

Figures 8A, 8B, 8C, 8D:
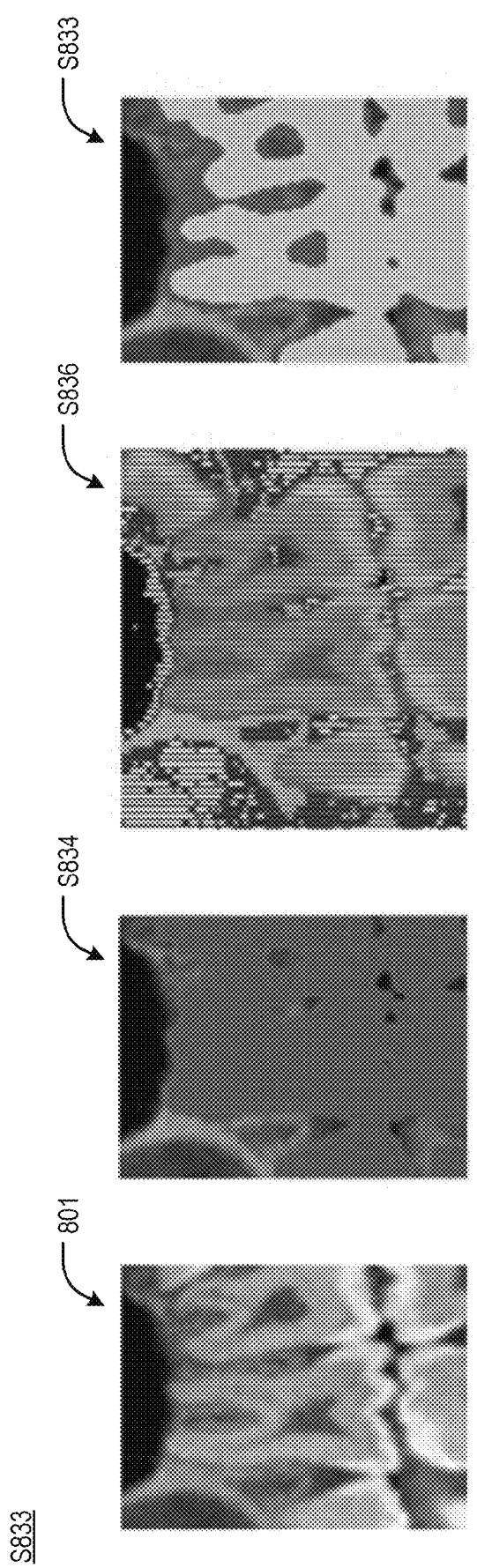
FIG. 8A is an illustration of an aspect of a snakes segmentation of a dental image processing protocol, according to an embodiment of the present disclosure.
FIG. 8B is an illustration of an aspect of a snakes segmentation of a dental image processing protocol, according to an embodiment of the present disclosure.
FIG. 8C is an illustration of an aspect of a snakes segmentation of a dental image processing protocol, according to an embodiment of the present disclosure.
FIG. 8D is an illustration of an aspect of a snakes segmentation of a dental image processing protocol, according to an embodiment of the present disclosure.

Following training, the retrained CNN classifier may be applied to a second dataset comprising a plurality of CBCT dental images. FIG. 8A, FIG. 8B, FIG. 8C, and FIG. 8D are illustrations of aspects of a snakes segmentation of a dental image processing protocol, according to an embodiment of the present disclosure. In order to prepare the retrained CNN classifier predictions for snakes segmentation S833, the predictions, generated for a source image 801, for instance, shown in FIG. 8A, may first be converted to segmentations. The segmented predictions S834, shown in FIG. 8B, may then be downsampled to obtain images prepared for snakes segmentation S835. To this end, pixels of the dental images may then be thresholded according to HU S836, shown in FIG. 8C, wherein HU values reflect the radiodensity of a tissue and similar hues indicate similar tissue types. A Gaussian model estimator may provide a speed map for snakes segmentation. The above-described snakes segmentation may then be performed as a final segmentation of the modified output of the retrained CNN classifier S833, as shown in FIG. 8D.

The resulting plurality of CBCT dental images segmented via snakes segmentation form an initial FCN training database. The initial FCN training database can then be used to retrain a pretrained Unet-FCN.

Figure 9:
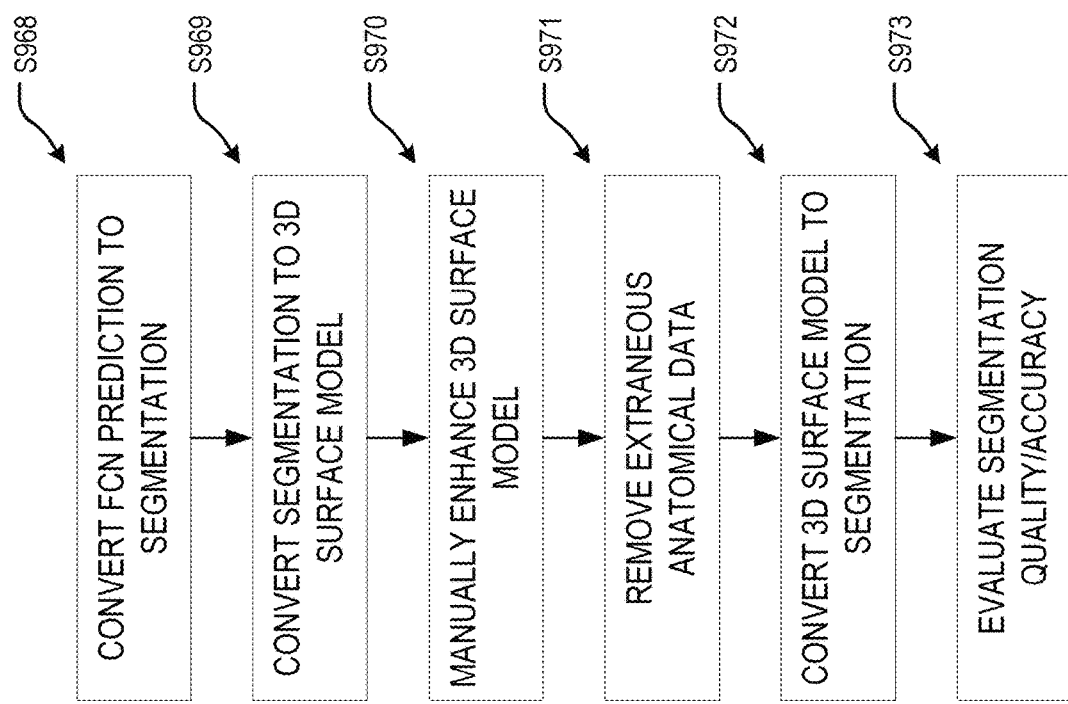
FIG. 9 is a flowchart of an aspect of a training data generation protocol, according to an embodiment of the present disclosure.

As described above, and with reference to FIG. 9, predictions from the retrained FCN classifier may be evaluated and improved via a 3D model enhancement. FIG. 9 is a flowchart of an aspect of a training data generation protocol, according to an embodiment of the present disclosure, wherein the predictions from the retrained FCN classifier may be improved via enhancement of a 3D model. First, predictions of the initial FCN training database from the retrained FCN classifier may be segmented S968. These segmentations may then be converted to a 3D polygonal surface S969. This allows for enhancement of the 3D surface model S970 at a holistic level and with focus on the result, eliminating the need to enhance individual slices of the model. In an example, this reduces computational burden from five-hundred 2D slices to one 3D polygonal surface. Having improved the 3D surface model by applying filters and correcting prediction errors, extraneous anatomical data may then be removed from the 3D surface model S971 in order to isolate anatomical features of interest. Once 'enhanced', the 3D surface model can be reverted to segmentation S972. Segmentations may then be confirmed for quality S973, relative to a pre-determined error threshold, and added to a subsequent FCN training database if of sufficient quality.

Figure 3:
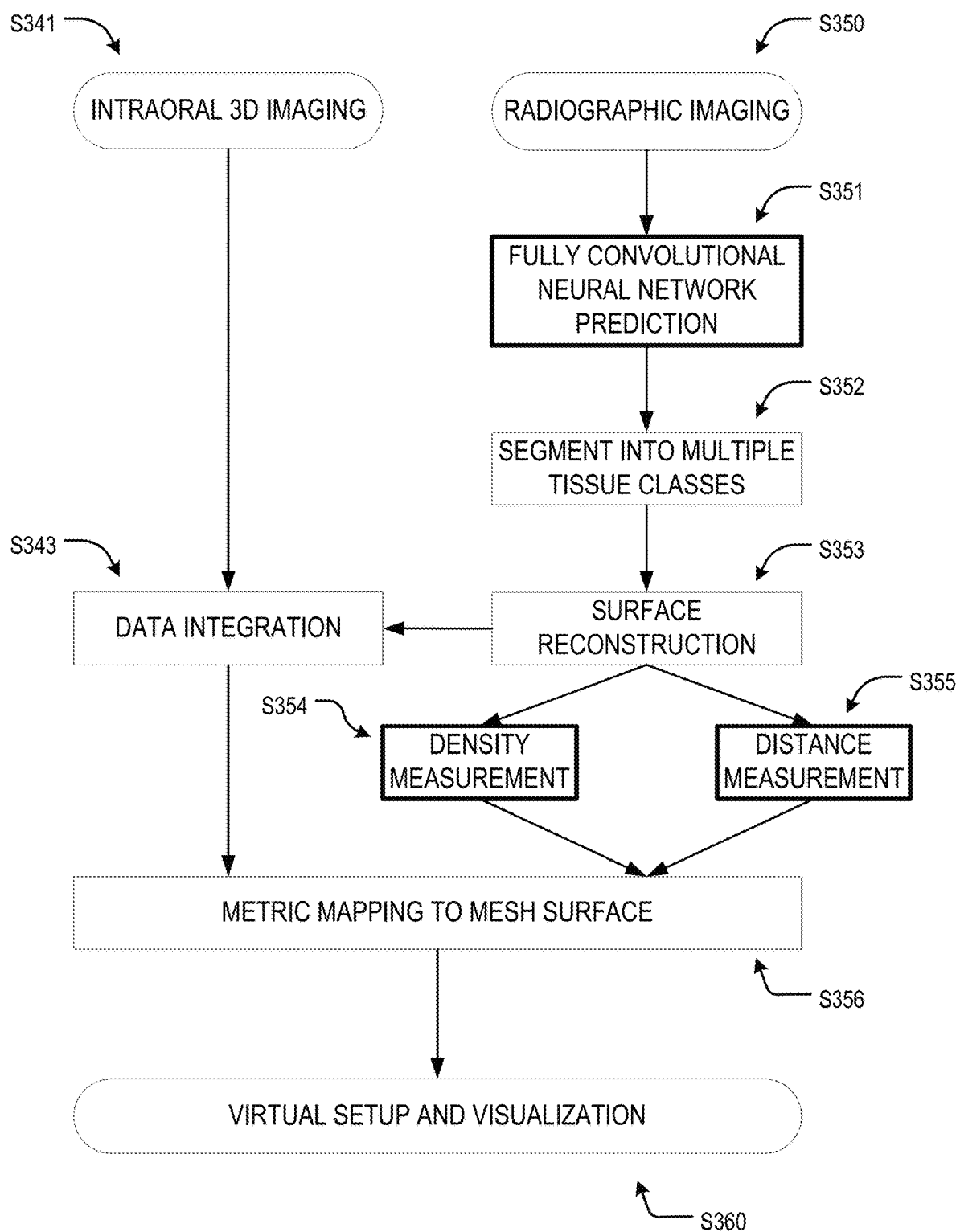
FIG. 3 is a flowchart of a dental image processing protocol, according to an embodiment of the present disclosure.
Figures 10A, 10B, 10C:
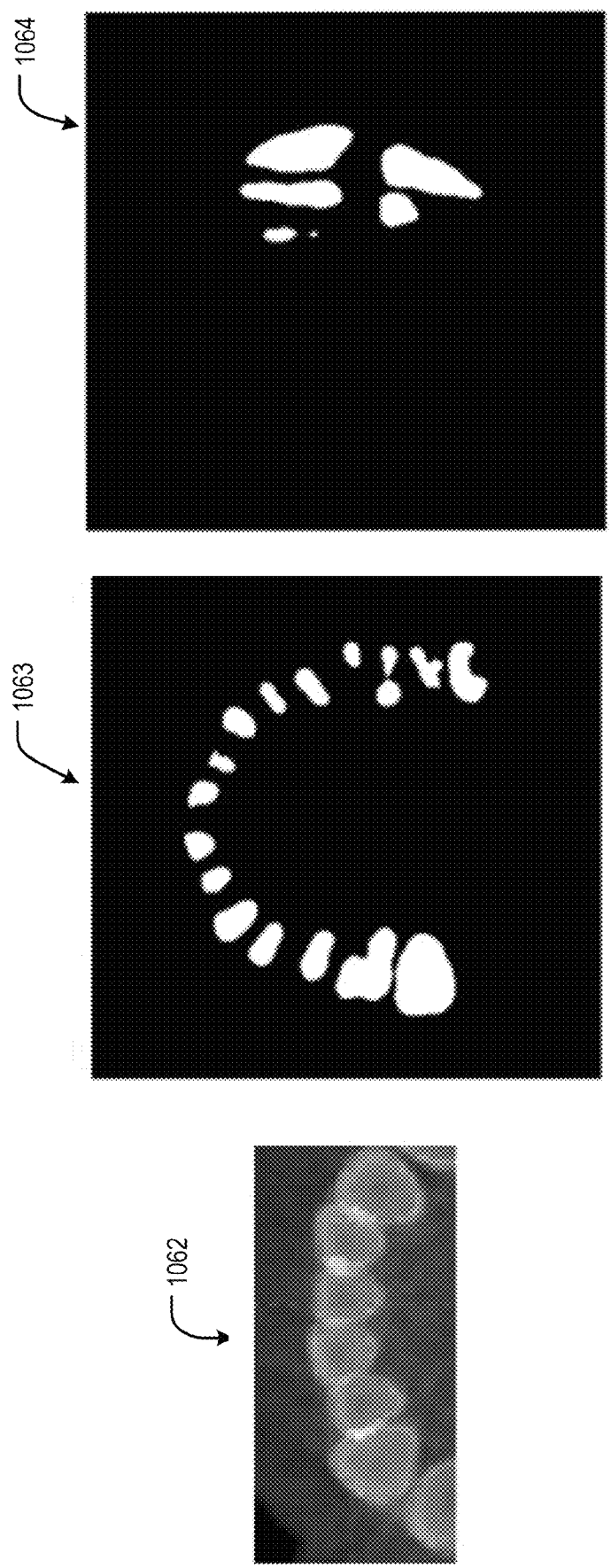
FIG. 10A is an illustration of a segmentation of teeth of a dental image, according to an embodiment of the present disclosure.
FIG. 10B is an illustration of a segmentation of teeth of a dental image, according to an embodiment of the present disclosure.
FIG. 10C is an illustration of a segmentation of teeth of a dental image, according to an embodiment of the present disclosure.

Following enhancement of CBCT dental images of the subsequent FCN training database, as described above, and retraining of the retrained FCN classifier, the run-time in FIG. 3 may be implemented with the retrained FCN classifier. FIG. 10A, FIG. 10B, and FIG. 10C are illustrations of a segmentation of teeth of a dental image after prediction by the retrained FCN classifier. In FIG. 10A, an illustration of a segmentation of an anterior aspect of a dental arch from a CBCT dental image, according to an embodiment of the present disclosure, a transverse plane segmentation 1062 with overlaid 'tooth' predictions is observed. A full dental arch segmentation in a transverse plane 1063, in FIG. 10B, illustrates a segmented FCN classifier prediction across a cross-section of the dental arch, highlighting the crowns of each tooth. In a sagittal plane view of an aspect of a superior, or upper, and an inferior, or lower, dental arch 1064, in FIG. 10C, a complete view of a cross-section of an aspect of each dental arch is visible, including crowns and roots.

Conversely, FIG. 11A, FIG. 11B, and FIG. 11C are illustrations of a segmentation of bone of a dental image after prediction by the retrained FCN classifier, according to an embodiment of the present disclosure. After applying the retrained FCN classifier to an unknown source image 1101, for instance, shown in FIG. 11A, a sagittal view of the mouth of a patient, wherein the skull is on the left side of the image, a 'bone' classification is predicted. Follow classification of 'bone', continuous regions of 'bone' may be identified and relative centers of mass may be compared to determine anatomic identity, in the context of the dental image plane. As shown in FIG. 11B, a contiguous region of classified 'bone' proximate to the skull, or anatomically superior, is identified as the maxilla 1165, while an inferior contiguous region is identified as the mandible 1166, as shown in FIG. 11C.

Figures 12A, 12B:
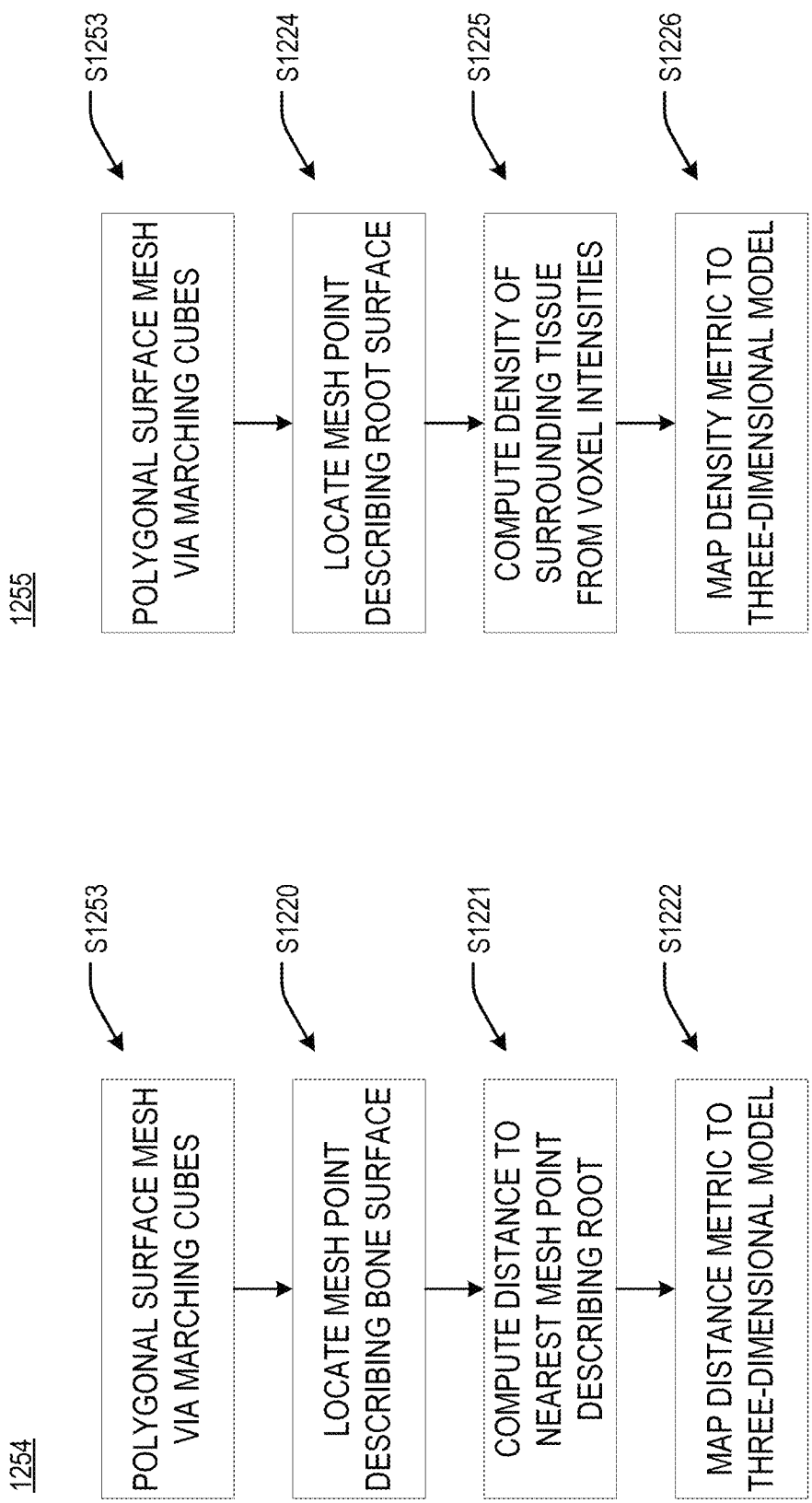
FIG. 12A is a flowchart of a determination of a distance metric of a three-dimensional model, according to an embodiment of the present disclosure.
FIG. 12B is a flowchart of a determination of a density metric of a three-dimensional model, according to an embodiment of the present disclosure.

A plurality of processed CBCT dental images generated via prediction by the retrained FCN classifier, similar to those observed in FIG. 10A through FIG. 11C, can be segmented and reconstructed to render a complex 3D model of dentition in the context of periodontal tissues, as reflected in FIG. 4. To this end, following rendering of the segmentation of the above-described predictions via the retrained FCN classifier, the resulting simple 3D model may be further enhanced to provide additional information related to the periodontal tissue environment. From the simple 3D model generated via marching cubes, for instance, a density measurement and distance measurement can be performed. FIG. 12A and FIG. 12B are flowcharts of a determination of a distance measurement and a density measurement of a three-dimensional model, respectively, according to an embodiment of the present disclosure. To this end, the density measurement 1254 and the distance measurement 1255 of the periodontal space may be computed from the surface reconstruction of the segmented predictions of the retrained FCN classifier S1253.

The distance measurement 1254 comprises locating and computing, for each point on the surface reconstruction describing the surface of a bone S1220, a distance to a nearest point on the surface reconstructions describing the root S1221. This distance, therefore, reflects a volume of alveolar process wherein a tooth may move.

The density measurement comprises locating and computing, from each point on a surface reconstruction describing the surface of a root S1224, a metric of the density of the surrounding tissue S1225. This metric may be determined on the basis of mean voxel intensities surrounding a vertex-point coordinate of the surface reconstruction, reflecting the spatial arrangement of bone and the ability of a tooth to move, therein.

Once calculated for each point within the surface reconstruction, or simple 3D model, the density measurement S1226 and distance measurement S1222 may be mapped to the simple 3D model, rendering it a complex 3D model. To allow for rapid visualization of the distance measurement, with reference again to FIG. 4, varying distances are denoted via heat map, wherein regions of minimal thickness and maximal thickness are of varying hues.

Figure 13B:
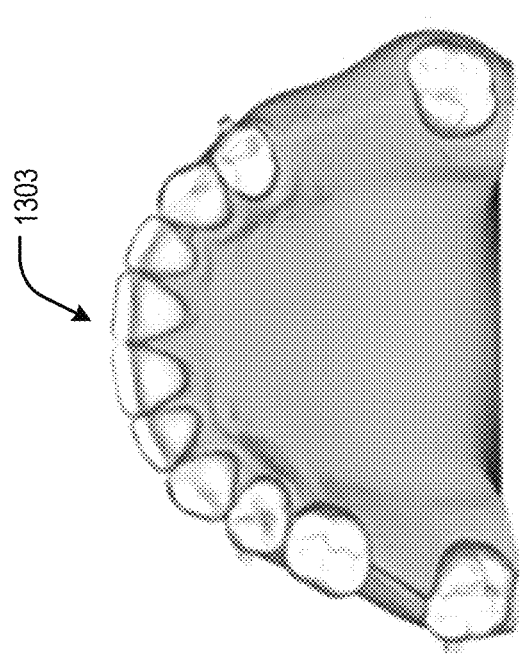
FIG. 13B is an illustration of a three-dimensional model of dentition, according to an embodiment of the present disclosure.
Figure 13A:
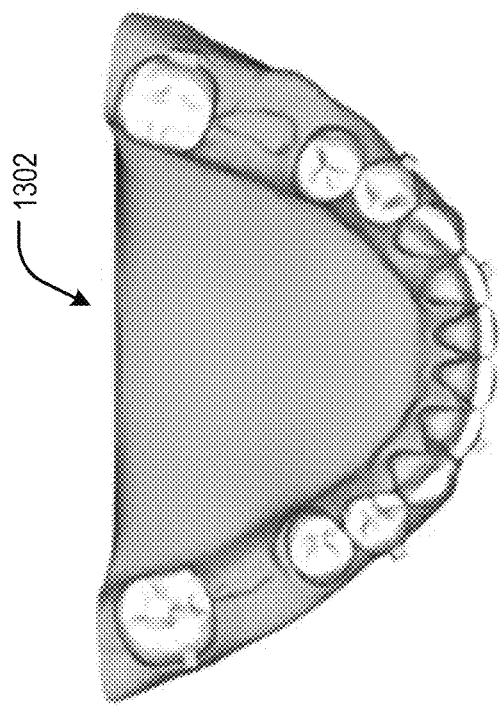
FIG. 13A is an illustration of a three-dimensional model of dentition, according to an embodiment of the present disclosure.

Having generated a 'color' mapped complex 3D model of an initial tooth position of dentition of a patient, virtual setup and visualization of intermediary tooth movements during realignment can be envisioned. In an embodiment, a dental professional can prescribe a final tooth position for each tooth of each dental arch. Further, this final tooth position can be determined in context of a control arrangement, or dentition, shown in FIG. 13A and FIG. 13B. FIG. 13A and FIG. 13B are illustrations of a three-dimensional model of dentition, according to an embodiment of the present disclosure. An inferior dental arch 1302, shown in FIG. 13A, and superior dental arch 1303, shown in FIG. 13B, represent an optimal crown position. Using the dental control and optimal crown positions of FIG. 13A and FIG. 13B, a tooth movement plan can be developed.

Specifically, as shown in FIG. 14A, FIG. 14B, and FIG. 14C, illustrations of a positioning of a three-dimensional model generated from a processed dental image, intermediary stages of tooth movement can be determined based upon a prescribed final tooth position and an initial tooth position. The initial tooth position 1475 in FIG. 14A reflects a maligned dental arch and the varying thicknesses of alveolar process surrounding the root of the tooth. In an example, the roots of a lateral incisor are deep to the buccal surface of the alveolar process, whereas an adjacent tooth, or a central incisor, may be relatively superficial with respect to the buccal surface of the alveolar process. In an embodiment, a prescribing dental professional determines that a lateral incisor, indicated by the left arrow of the initial tooth alignment 1475, need be rotated about a transverse axis, the roots of the lateral incisor being moved anteriorly and proximate to the buccal surface of the alveolar process. At an intermediary stage 1476, shown in FIG. 14B, with the left arrow still indicating the lateral incisor, the required movement has been initiated. The changing hue of the model proximate the roots of the lateral incisor reflect this movement. Following subsequent intermediary movements, a final tooth position 1477, shown in FIG. 14C, may be achieved. Consequently, the determined thickness of the alveolar process between the root surface and the buccal surface of the alveolar process is decreased, as indicated by the shifting hue at the left arrow of the complex 3D model of FIG. 14C.

According to an embodiment, intermediary tooth positions may be determined manually according to a final tooth position, an initial tooth position, and the movements of adjacent teeth. In another embodiment, intermediary tooth positions may be determined automatically, via a path determining protocol executed by the processing circuitry.

In another embodiment, determined tooth movements may be informed by a quantitative model of expected bone growth and resorption at the root, lingual, and buccal surfaces of the alveolar process. For example, as a tooth movement results in anterior rotation of a root of a tooth, bone deposition, and thus thickening, may occur on the buccal surface of the alveolar process. Concurrently, bone resorption may occur on the lingual surface of the alveolar process. Expected bone growth or bone resorption can be added to the complex 3D model of the teeth and surrounding bone during rendering of intermediary tooth movements.

In still another embodiment, upon evaluation of a complex 3D model, a prescribed final tooth position may not be a realizable final tooth position due to constraints of the facial skeleton, as informed by the above-described density measurement and distance measurement. In such case, a realizable final tooth position is determined, with the input of the prescribing dental professional, and in the context of function and aesthetic.

Having determined intermediary and final tooth positions, and with reference again to FIG. 1, dental aligners may be fabricated, accordingly.

Figure 15:
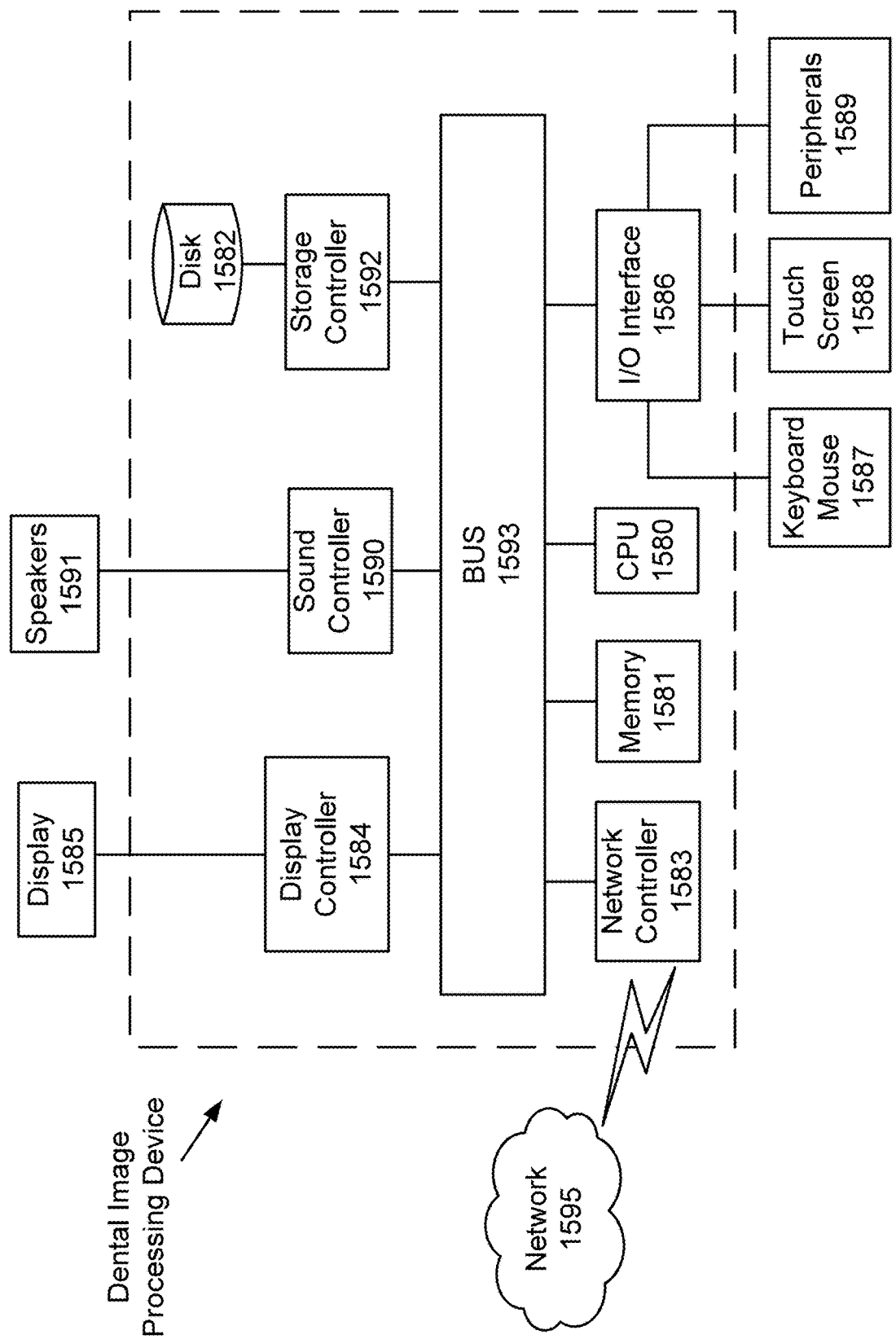
FIG. 15 is a schematic of exemplary hardware for implementation of a dental image processing protocol, according to an embodiment of the present disclosure.

Next, a hardware description of the dental image processing device according to exemplary embodiments is described with reference to FIG. 15. In FIG. 15, the dental image processing device includes a CPU 1580 which performs the processes described above/below. In another embodiment, the processing device may be a GPU, GPGPU, or TPU. The process data and instructions may be stored in memory 1581. These processes and instructions may also be stored on a storage medium disk 1582 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the dental image processing device communicates, such as a server or computer.

Further, the claimed advancements may be provided as a utility application, background daemon, or component of an operating system, or combination thereof, executing in conjunction with CPU 1580 and an operating system such as Microsoft Windows 7, UNIX, Solaris, LINUX, Apple MAC-OS and other systems known to those skilled in the art.

The hardware elements in order to achieve the dental image processing device may be realized by various circuitry elements, known to those skilled in the art. For example, CPU 1580 may be a Xenon or Core processor from Intel of America or an Opteron processor from AMD of America, or may be other processor types that would be recognized by one of ordinary skill in the art. Alternatively, the CPU 1580 may be implemented on an FPGA, ASIC, PLD or using discrete logic circuits, as one of ordinary skill in the art would recognize. Further, CPU 1580 may be implemented as multiple processors cooperatively working in parallel to perform the instructions of the inventive processes described above.

The dental image processing device in FIG. 15 also includes a network controller 1583, such as an Intel Ethernet PRO network interface card from Intel Corporation of America, for interfacing with network 1595. As can be appreciated, the network 1595 can be a public network, such as the Internet, or a private network such as an LAN or WAN network, or any combination thereof and can also include PSTN or ISDN sub-networks. The network 1595 can also be wired, such as an Ethernet network, or can be wireless such as a cellular network including EDGE, 3G and 4G wireless cellular systems. The wireless network can also be WiFi, Bluetooth®, or any other wireless form of communication that is known.

The dental image processing device further includes a display controller 1584, such as a NVIDIA GeForce GTX® or Quadro® graphics adaptor from NVIDIA Corporation of America for interfacing with display 1585, such as a Hewlett Packard HPL2445w® LCD monitor. A general purpose I/O interface 1586 interfaces with a keyboard and/or mouse 1587 as well as a touch screen panel 1588 on or separate from display 1585. General purpose I/O interface also connects to a variety of peripherals 1589 including printers and scanners, such as an OfficeJet® or DeskJet® from Hewlett Packard.

A sound controller 1590 is also provided in the dental image processing device, such as Sound Blaster X-Fi Titanium from Creative, to interface with speakers/microphone 1591 thereby providing sounds and/or music.

The general purpose storage controller 1592 connects the storage medium disk 1582 with communication bus 1593, which may be an ISA, EISA, VESA, PCI, or similar, for interconnecting all of the components of the dental image processing device. A description of the general features and functionality of the display 1585, keyboard and/or mouse 1587, as well as the display controller 1584, storage controller 1592, network controller 1583, sound controller 1590, and general purpose I/O interface 1586 is omitted herein for brevity as these features are known.

Embodiments of the present disclosure may also be as set forth in the following parentheticals.

(1) A method for generating an intermediate position of one or more teeth of a dental arch of a patient, comprising classifying, via processing circuitry, pixels of one or more medical images into classes corresponding to biological structure types, segmenting, via the processing circuitry, the classified pixels of the one or more medical images into biological structures, rendering, via the processing circuitry, a three-dimensional model of the biological structures based on the segmented classified pixels, determining, via the processing circuitry, one or more metrics, based upon the three-dimensional model, describing characteristics of a bone of the biological structures, acquiring, via the processing circuitry, a final position of each of the one or more teeth of the dental arch based upon the three-dimensional model, and generating, via the processing circuitry, the intermediate position of each of the one or more teeth of the patient based upon the one or more metrics and the acquired final position.

(2) The method according to (1), wherein the classifying further comprises training, via the processing circuitry, a classifier on a training database, and classifying, via the processing circuitry, the pixels of the one or more medical images based upon the classifier, wherein the training database includes a corpus of reference medical images, each reference medical image comprising at least one identifiable reference biological structure associated in the training database with at least one corresponding description of the biological structure type.

(3) The method according to either (1) or (2), wherein the intermediate position of each of the one or more teeth is determined based upon a position of an aspect of a proximate tooth of the one or more teeth of the dental arch.

(4) The method according to any of (1) to (3), wherein the training further comprises training, via the processing circuitry, a first neural network according to a first dataset, training, via the processing circuitry, a second neural network according to a second dataset, the second dataset comprising a plurality of classification predictions of the first neural network, and generating, via the processing circuitry, the training database based upon a plurality of classification predictions of the second neural network.

(5) The method according to any of (1) to (4), wherein the second neural network is a fully convolutional neural network.

(6) The method according to any of (1) to (5), wherein one of the one or more metrics is a distance metric, the distance metric being defined as a distance between a surface of a root of one of the one or more teeth of the dental arch and a surface of an alveolar process.

(7) The method according to any of (1) to (6), wherein one of the one or more metrics is a density metric, the density metric being defined as a measure of mean intensity of voxels adjacent to a central voxel.

(8) A non-transitory computer-readable storage medium storing computer-readable instructions that, when executed by a computer having a processing circuitry, cause the computer to perform a method, the method comprising classifying pixels of one or more medical images into classes corresponding to biological structure types, segmenting the classified pixels of the one or more medical images into biological structures, rendering a three-dimensional model of the biological structures based on the segmented classified pixels, determining one or more metrics, based upon the three-dimensional model, describing characteristics of a bone of the biological structures, acquiring a final position of each of the one or more teeth of the dental arch based upon the three-dimensional model, and generating the intermediate position of each of the one or more teeth of the patient based upon the one or more metrics and the acquired final position.

(9) The method according to (8), wherein the classifying further comprises training a classifier on a training database, and classifying the pixels of the one or more medical images based upon the classifier, wherein the training database includes a corpus of reference medical images, each reference medical image comprising at least one identifiable reference biological structure associated in the training database with at least one corresponding description of the biological structure type.

(10) The method according to either (8) or (9), wherein the intermediate position of each of the one or more teeth is determined based upon a position of an aspect of a proximate tooth of the one or more teeth of the dental arch.

(11) The method according to any of (8) to (10), wherein the training further comprises training a first neural network according to a first dataset, training a second neural network according to a second dataset, the second dataset comprising a plurality of classification predictions of the first neural network, and generating the training database based upon a plurality of classification predictions of the second neural network.

(12) The method according to any of (8) to (11), wherein the second neural network is a fully convolutional neural network.

(13) The method according to any of (8) to (12), wherein one of the one or more metrics is a distance metric, the distance metric being defined as a distance between a surface of a root of one of the one or more teeth of the dental arch and a surface of an alveolar process.

(14) The method according to any of (8) to (13), wherein one of the one or more metrics is a density metric, the density metric being defined as a measure of mean intensity of voxels adjacent to a central voxel.

(15) An apparatus for processing of dental images, comprising a processing circuitry configured to classify pixels of one or more medical images into classes corresponding to biological structure types, segment the classified pixels of the one or more medical images into biological structures, render a three-dimensional model of the biological structures based on the segmented classified pixels, determine one or more metrics, based upon the three-dimensional model, describing a bone of the biological structures, acquire a final position of each of the one or more teeth of the dental arch based upon the three-dimensional model, and generate the intermediate position of each of the one or more teeth of the patient based upon the one or more metrics and the acquired final position.

(16) The apparatus according to (15), wherein the processing circuitry is further configured to train a classifier on a training database, and classify the pixels of the one or more medical images based upon the classifier, wherein the training database includes a corpus of reference medical images, each reference medical image comprising at least one identifiable reference biological structure associated in the training database with at least one corresponding description of the biological structure type.

(17) The apparatus according to either (15) or (16), wherein the intermediate position of each of the one or more teeth is determined based upon a position of an aspect of a proximate tooth of the one or more teeth of the dental arch.

(18) The apparatus according to any of (15) to (17), wherein the training further comprises training a first neural network according to a first dataset, training a second neural network according to a second dataset, the second dataset comprising a plurality of classification predictions of the first neural network, and generating the training database based upon a plurality of classification predictions of the second neural network.

(19) The apparatus according to any of (15) to (18), wherein one of the one or more metrics is a distance metric, the distance metric being defined as a distance between a surface of a root of one of the one or more teeth of the dental arch and a surface of an alveolar process.

(20) The apparatus according to any of (15) to (19), wherein one of the one or more metrics is a density metric, the density metric being defined as a measure of mean intensity of voxels adjacent to a central voxel.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Numerous modification and variations on the present invention are possible in light of the above teachings. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

All publications, patent applications, patents, and other references mentioned herein are incorporated by reference in their entirety. Further, the materials, methods, and examples are illustrative only and are not intended to be limiting, unless otherwise specified.

The invention claimed is:

1. A method for generating an intermediate position of one or more teeth of a dental arch of a patient, comprising:
classifying, via processing circuitry, pixels of one or more medical images into classes corresponding to biological structure types;
segmenting, via the processing circuitry, the classified pixels of the one or more medical images into biological structures;
rendering, via the processing circuitry, a three-dimensional model of the biological structures based on the segmented classified pixels;
determining, via the processing circuitry, one or more metrics, based upon the three-dimensional model, describing characteristics of the biological structures;

acquiring, via the processing circuitry, a final position of each of the one or more teeth of the dental arch of the patient based upon the three-dimensional model; and generating, via the processing circuitry, the intermediate position of each of the one or more teeth of the dental arch of the patient based upon the one or more metrics and the acquired final position, wherein one of the one or more metrics is a distance metric defined as a distance between a surface of a root of one of the one or more teeth of the dental arch of the patient and a surface of a neighboring biological structure of the three-dimensional model, or a density metric defined as a measure of mean intensity of voxels adjacent to a central voxel.

2. The method according to claim 1, wherein the classifying further comprises training, via the processing circuitry, a classifier on a training database; and classifying, via the processing circuitry, the pixels of the one or more medical images based upon the classifier, wherein the training database includes a corpus of reference medical images, each reference medical image comprising at least one identifiable reference biological structure associated in the training database with at least one corresponding description of a biological structure type.

3. The method according to claim 2, wherein the training further comprises training, via the processing circuitry, a first neural network according to a first dataset;

training, via the processing circuitry, a second neural network according to a second dataset, the second dataset comprising a plurality of classification predictions of the first neural network; and generating, via the processing circuitry, the training database based upon a plurality of classification predictions of the second neural network.

4. The method according to claim 3, wherein the second neural network is a fully convolutional neural network.

5. The method according to claim 1, wherein the intermediate position of each of the one or more teeth of the dental arch of the patient is determined based upon a position of an aspect of a neighboring tooth of the one or more teeth of the dental arch of the patient.

6. The method according to claim 1, wherein the surface of the neighboring biological structure of the three-dimensional model is a surface of an alveolar process.

7. An apparatus for processing of dental images, comprising:

processing circuitry configured to classify pixels of one or more medical images into classes corresponding to biological structure types;

segment the classified pixels of the one or more medical images into biological structures;

render a three-dimensional model of the biological structures based on the segmented classified pixels;

determine one or more metrics, based upon the three-dimensional model, describing characteristics of the biological structures;

acquire a final position of each of one or more teeth of a dental arch of a patient based upon the three-dimensional model; and generate an intermediate position of each of the one or more teeth of the dental arch of the patient based upon the one or more metrics and the acquired final position, wherein one of the one or more metrics is a distance metric defined as a distance between a surface of a root of one of the one or more teeth of the dental arch of the patient and a surface of a neighboring biological structure of the three-dimensional model, or a density metric defined as a measure of mean intensity of voxels adjacent to a central voxel.

8. The apparatus according to claim 7, wherein the processing circuitry is further configured to train a classifier on a training database; and classify the pixels of the one or more medical images based upon the classifier, wherein the training database includes a corpus of reference medical images, each reference medical image comprising at least one identifiable reference biological structure associated in the training database with at least one corresponding description of a biological structure type.

9. The apparatus according to claim 8, wherein the training further comprises training a first neural network according to a first dataset;

training a second neural network according to a second dataset, the second dataset comprising a plurality of classification predictions of the first neural network; and generating the training database based upon a plurality of classification predictions of the second neural network.

10. The apparatus according to claim 7, wherein the intermediate position of each of the one or more teeth of the dental arch of the patient is determined based upon a position of an aspect of a neighboring tooth of the one or more teeth of the dental arch of the patient.

11. The apparatus according to claim 7, wherein the surface of the neighboring biological structure of the three-dimensional model is a surface of an alveolar process.

* * * * *